(12) United States Patent
Black, Jr.

(10) Patent No.: US 6,323,003 B1
(45) Date of Patent: Nov. 27, 2001

(54) COMPOSITIONS AND METHODS FOR ACTIVATING GENES OF INTEREST

(76) Inventor: Charles Allen Black, Jr., 1139 Judy Ann Pl., Pittsburgh, PA (US) 15237

( * ) Notice: Subject to any disclaimer, the term of this patent is extended or adjusted under 35 U.S.C. 154(b) by 0 days.

(21) Appl. No.: 09/446,402

(22) PCT Filed: Jun. 24, 1998

(86) PCT No.: PCT/US98/13093

§ 371 Date: Dec. 20, 1999

§ 102(e) Date: Dec. 20, 1999

(87) PCT Pub. No.: WO98/58944

PCT Pub. Date: Dec. 30, 1998

Related U.S. Application Data

(60) Provisional application No. 60/050,772, filed on Jun. 25, 1997.

(51) Int. Cl.[7] .............................. C07H 21/04; C12N 15/00
(52) U.S. Cl. ..................... 435/69.1; 435/6; 435/320.1; 435/375; 435/377; 536/23.1; 536/24.1; 536/24.5; 514/44
(58) Field of Search ........................ 435/6, 320.1, 375, 435/377; 536/23.1, 24.1, 24.5; 514/44

(56) References Cited

PUBLICATIONS

W. French Anderson, "Human gene therapy", Nature, vol. 392, pp. 25–30, 1998.*
Inder M. Verma and Nikunj Somia, "Gene therapy –promises, problems and prospects", Nature, vol. 389 239–242, 1997.*
Andrea D. Branch, "A good antisense molecule is hard to find", Elsevier Ltd. pp. 45–50, 1998.*
Hirashima et al. *Engineering of the m–RNA–Interfering complementary RNA Immune System Against Viral Infection*; Proceeding of the National Academy of Sciences, USA. Oct. 1986, pp. 7726–7730, vol. 83.
Coleman et al. *The Use of RNA's Complementary to Sepcific mRNAs to Regulate the Expression of Individual Bacterial Genes*. Cell, Jun. 1984, pp. 429–435, vol. 37.

* cited by examiner

*Primary Examiner*—Sean McGarry
(74) *Attorney, Agent, or Firm*—Alston & Bird LLP

(57) ABSTRACT

Compositions and methods for activating genes of interest are provided. The compositions comprise a masked targeted expression cassette which expresses a gene product only in the presence of a target molecule. The cassettes are useful for the treatment of disease and for preventing the proliferation of neoplastic cells.

4 Claims, 8 Drawing Sheets

COMPOSITIONS AND METHODS FOR ACTIVATING GENES OF INTEREST

RELATED APPLICATIONS

This application claims the benefit of U.S. Provisional Application No. 60/050,772 filed Jun. 25, 1997.

FIELD OF THE INVENTION

The present invention relates to methods and compositions for activating genes of interest particularly in the presence of a target gene.

BACKGROUND OF THE INVENTION

The nature of and basic approaches to cancer treatment are constantly changing. At present, adjuvant chemotherapy routinely follows local treatment of cancers. Clinical protocols are now exploring genetic therapies, manipulations of the immune system, stimulation of normal hematopoietic elements, induction of differentiation in tumor tissues, and inhibition of angiogenesis. Research in these new areas has led to applications for nonmalignant disease.

At the same time, the new clinical protocols have a narrow therapeutic index as well as a great potential for causing harmful side effects. A thorough understanding of the pharmacology, drug interactions, and clinical pharmacokinetics is essential for safe and effective use in human beings.

The therapy of viral infection is in its infancy. Bacterial infection is typically treated with agents, such as antibiotics, which take advantage of the differences in metabolism between the infecting organism and its host. However, viruses largely employed the host's own enzymes to effect the replication, and thus leave few opportunities for pharmacological intervention. By employing strong regulatory elements, the virus obtains transcription and translation of its own genes at the expense of host genes.

In mammals, viral infection is combatted naturally by cytotoxic T-lymphocytes, which recognize viral proteins when expressed on the surface of host cells, and lyse the infected cells. Destruction of the infected cell prevents the further replication of the virus. Other defenses include the expression of interferon, which inhibits protein synthesis and viral budding, and expression of antibodies, which remove free viral particles from body fluids. However, induction of these natural mechanisms require exposure of the viral proteins to the immune system. Many viruses exhibit a dormant or latent phase, during which little or no protein synthesis is conducted. The viral infection is essentially invisible to the immune system during such phases.

Retroviruses carry the infectious form of their genome in the form of a strand of RNA. Upon infection, the RNA genome is reverse-transcribed into DNA and is typically then integrated into the host's chromosomal DNA at a random site. On occasion integration occurs at a site which truncates a gene encoding an essential cellular receptor or growth factor, or which places such a gene under control of the strong viral cis-acting regulatory element, which may result in transformation of the cell into a malignant state.

Viruses may also be oncogenic due to the action of their trans-acting regulatory factors on host cell regulatory sequences. In fact, oncogenesis was the characteristic which led to the discovery of the first known retroviruses to infect humans. HTLV-I and HTLV-II (human T-lymphotrophic viruses I and II) were identified in the blood cells of patients suffering from adult T-cell leukemia (ATL), and are believed to induce neoplastic transformation by the action of their transactivating factors on lymphocyte promoter regions. Two additional retroviruses have been found to infect humans. These viruses, HIV-I and HIV-II, are the etiological agents AIDS.

Current therapy for HIV infection includes new drugs called protease inhibitors. These drugs can dramatically reduce HIV levels in the blood when taken with other antiviral compounds such as AZT. At the same time, natural weapons in the immune systems's defenses polypeptide molecules called chemokines, have been unveiled as potent foes of HIV.

Antisense oligodeoxynucleotides have been proposed as a major class of new pharmaceuticals. In general, antisense refers to the use of small, synthetic oligonucleotides resembling single-stranded DNA, to inhibit gene expression. Gene expression is inhibited through hybridization to coding (sense) sequences in a specific messenger RNA (mRNA) target by Watson-Crick base pairing in which adenosine and thymidine or guanosine and cytidine interact through hydrogen bonding.

Following the simple base-pairing rules which govern the interaction between the antisense oligodeoxynucleotides and the cellular RNA, allow the design of molecules to target any gene of a known sequence. A major advantage of this strategy is the potential specificity of action. In principal, an antisense molecule can be designed to target any single gene within the entire human genome, potentially creating specific therapeutics for any disease in which the causative gene is known. As a result, there have been numerous applications of antisense oligodeoxynucleotide (ODN) activity for potential antiviral and anticancer applications.

Antisense ODNs offer the potential to block the expression of specific genes within cells. Despite numerous reports of apparent antisense inhibition of gene expression in cultured cells, only in a few cases has specific inhibition been rigorously demonstrated. In many studies, specificity has been inferred from the biological effects of antisense as compared to control ODNs, without measuring levels of target RNA or proteins to evaluate specificity. Unintended side-effects of antisense technology could potentially occur through a number of mechanisms.

The potential of oligonucleotides as modulators of gene expression is currently under intense investigation. Most of the efforts are focused on inhibiting the expression of targeted genes such as oncogenes or viral genes. The oligonucleotides are directed either against RNA (antisense oligonucleotides) or against DNA where they form triplex structures inhibiting transcription by RNA polymerase II. To achieve a desired effect, the oligonucleotides must promote a decay of the preexisting, undesirable protein by effectively preventing its formation de novo.

There is therefore a need for the development of new antisense methods that are more potent, reliable and specific than those used in previous studies.

SUMMARY OF THE INVENTION

Compositions and methods for activating the expression of a gene of interest is provided. The compositions are antisense masked expression cassettes which comprise a double stranded nucleotide sequence. A first strand comprises an armed expression cassette, i.e., an RNA molecule which codes for a protein of interest linked downstream of a flanking sequence and a translation initiation site operably inserted upstream of the RNA sequence. The flanking sequence encodes a target molecule. That is, the flanking sequence encodes a target gene or codes for RNA of interest. The flanking sequence corresponds to the "sense" strand of the target. A second nucleotide strand is also provided, capable of hybridizing to the flanking sequence of the first nucleotide sequence; i.e., the antisense strand. The antisense strand masks the translation initiation site when bound. The flanking sequence can be designed so that the antisense sequences do not share 100% homology with the flanking sequence. Thus, in the presence of a target nucleotide molecule, the antisense strand will favor complementary binding with the target. In this manner, the antisense strand will disassociate from the armed strand and pair with the target. Disassociation of the antisense strand unmasks the ribosome binding site allowing the armed cassette to be translated in the presence of the target.

The compositions find use in regulation of gene expression, treatment of disease, and for preventing the proliferation of neoplastic cells. Additionally, the compositions have a broad range of use in both plant and animal applications.

DETAILED DESCRIPTION OF THE INVENTION

The present invention now will be described more fully hereinafter with reference to preferred embodiments. This invention may, however, be embodied in many different forms and should not be construed as limited to the embodiments set forth herein; rather, these embodiments are provided so that this disclosure will convey the scope of the invention to those skilled in the art.

Compositions and methods for controlling the expression of a gene of interest is provided. Expression is regulated by the use of antisense oligonucleotides to a target molecule. In this manner, the gene of interest is expressed only in the presence of RNA or DNA corresponding to the target molecule.

Figure 1:
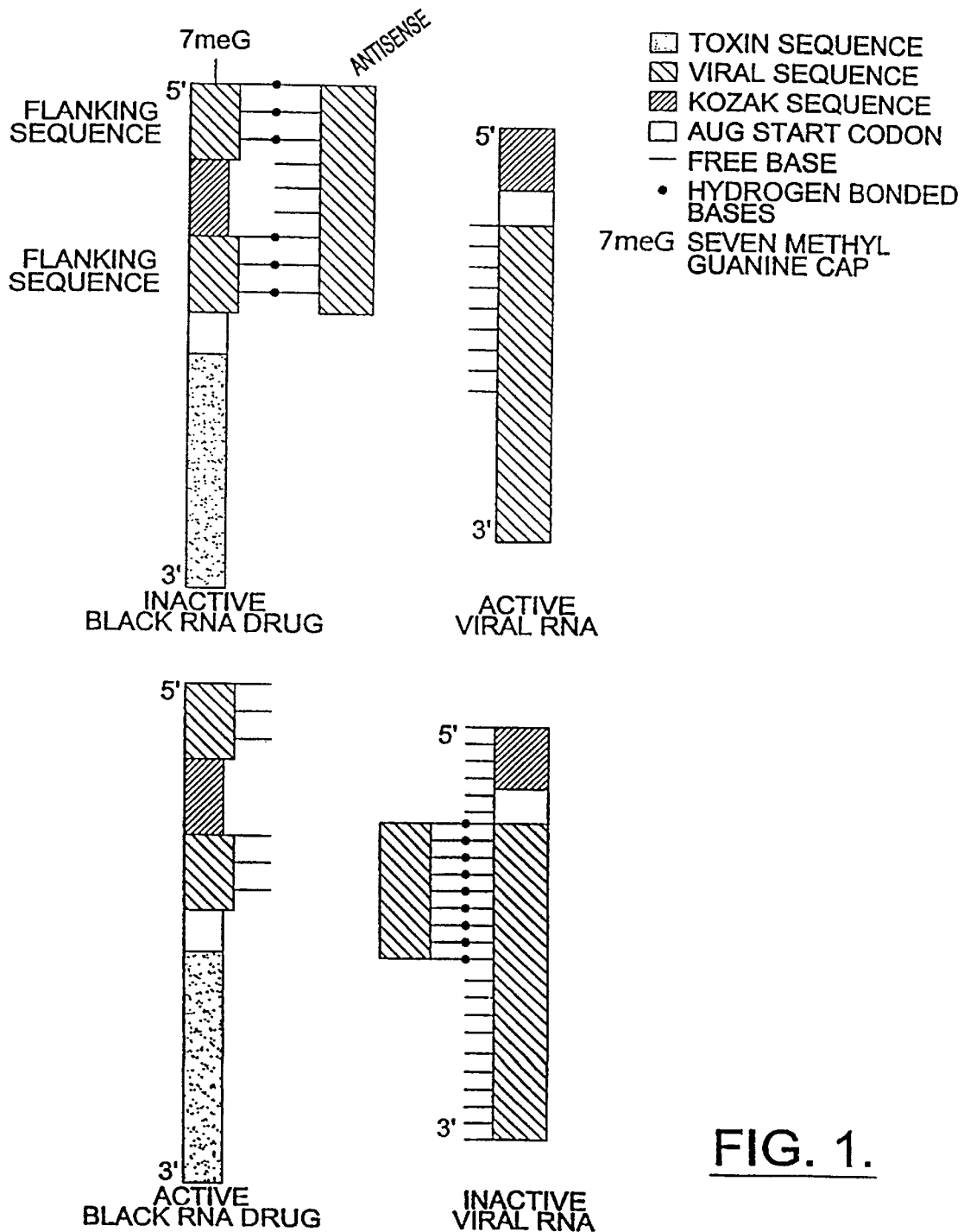
FIG. 1 provides a diagrammatic sketch of the masked targeted expression cassette as an antiviral drug.

The method involves the use of an antisense masked expression cassette. By antisense masked expression cassette is intended a double stranded nucleic acid molecule. The first strand comprises an RNA molecule for the protein of interest linked downstream of a flanking sequence. The flanking sequence comprises a nucleotide sequence the sense sequence, for a portion of the target gene. The first strand also comprises a translation initiation site downstream of the flanking sequence. It is recognized that the site of insertion for the ribosome binding site may vary. Optionally, a seven methyl guanine cap can be included to stabilize the molecule. See FIG. 1.

The second strand of the masked expression cassette comprises an antisense oligonucleotide corresponding to the target gene or sequence. That is, the antisense sequence is at least partially complementary to the target sequence comprised by the flanking sequence. The antisense oligonucleotide may be either an RNA molecule, a DNA molecule or mixtures thereof. The duplex formed by binding of the second antisense strand to the corresponding flanking sequence of the first strand excludes ribosomal scanning of the downstream sequences; including the translation initiation site, the sequence of interest, or both. Thus, translation and expression of the protein of interest is masked by the binding of the antisense strand to the flanking sequence. Displacement of the antisense strand from the flanking sequence unmasks expression and translation of the protein of interest.

The protein of interest will vary depending upon the use of the composition. For example, where the masked cassette is intended as a mechanism to inhibit the growth of neoplastic cells, the protein of interest is selected from toxin proteins, cytokines, cell regulators, or the like. Additionally, the RNA molecule may be non-coding RNA, such as RNA with RNAse activity.

A number of toxin proteins are known and can be used in the invention. These include ribosome inactivators, Pseudomonas exotoxin A (Chaudhary et al. (1990) *J. Biol Chem* 265:16303–16310); cell metabolism disruptors, such as ribonucleases (See, for example, Mariani et al. (1990) *Nature* 347:737–741); Barnase toxin, a chimeric toxin derived from Pseudomonas exotoxin A and a ribonuclease (Prior et al. (1990), *Cell* 64:1017–1023); Pertussis (Accession M14378 M16494, Micosia et al. (1986) *Proc. Natl. Acad. Sci. USA* 83:4631–4635); cholera (Dams et al. (1991) *Biochim. Biophys. Acta* 1090:139–141); Diphtheria, ricin (Gelfand et al. EP 0335476-A2); etc. Additionally, thymidine kinase from the herpes sequence may be used as a toxin or effector molecule. Transcription in a cell makes it susceptible to gancyclovir. Thus, the cells of interest could be labeled and then destroyed in a two step system.

The masked cassette comprising the above described toxin sequences can be used to target and destroy any cell, organ, organism or species; so long as a target sequence can be identified that is specific to that cell, organ, organism or species. For example, the cassette can be used to selectively target and eliminate vertebrate environmental pests. Such pests include agricultural pests including foxes and rabbits in Australia.

The cassette can be used to selectively destroy cells infected with viruses. In this aspect, the target sequence comprises a virus-specific sequence, while the protein of interest is a toxin as described above.

The masked cassette can be used to treat a variety of diseases. Such diseases include, but are not limited to, diseases involving an overactive organ, such as a hyperactive thyroid. In this aspect, the masked cassette comprises a thyroid-specific target sequence and a protein toxin as described above.

The cassette can be used to treat diseases involving a defective gene. In this aspect, the target sequence comprises the sequence of the defective mRNA, while the sequence of interest comprises the sequence of the normal protein. The intended affect can be twofold. The binding of the antisense strand to the defective mRNA can shut down the production of the defective protein, while expression of the sequence of interest results in production of the normal protein.

The cassette can be used to produce a protein of interest in an organ which lacks the protein. In this aspect, the target sequence comprises an organ-specific sequence, while the sequence of interest comprises the sequence of the protein lacking in that organ.

The invention is also useful in an assay system to determine the presence of a target molecule. In this instance the protein of interest will be a reporter protein that is easily detected, for example, by either a simple cytological stain or an enzyme assay. Such reporter sequences include but are not limited to beta galactosidase, chloramphenicol acetyltransferase (CAT), glucurodinase (GUS), and the like.

A translation initiation site is also included in the cassette. Such sequences are known in the art and include the Kozak sequence. See, for example Kozak, Marilyn (1988) *Mol. and Cell Biol.*, 8:2737–2744; Kozak, Marilyn (1991) *J. Biol. Chem.*, 266:19867–19870; Kozak, Marilyn (1990) *Proc Natl. Acad. Sci. USA*, 87:8301–8305; Kozak, Marilyn (1989) *J. Cell Biol.*, 108:229–241; and the references cited therein. Such references are herein incorporated by reference.

The translation initiation site can be inserted upstream of the sequence corresponding to the gene of interest. Kozak sequences can be designed that can initiate translation in all three reading frames. See, for example, Murphy and Efstratiadias (1987) *Proc. Natl. Acad. Sci. USA*, 84:8277–8281. Generally, the Kozak sequence will comprise the consensus sequence recognized for initiation in higher eukaryotes. Such consensus sequence is GCCGCC$_G^A$CCAUGG (SEQ ID NO: 18). This consensus sequence is repeated several times within the Kozak sequence to provide for the initiation of translation in all three reading frames.

The length of the Kozak sequence may vary. Generally, increasing the length of the leader sequence enhances translation.

It is recognized that a prokaryotic translation initiation site may also be used when appropriate; for example, when targeting a prokaryote. Such sequences include the Shine-Dalgarno sequence (UAAGGAGG (SEQ ID NO:19)), typically 5–10 bases upstream of the initiator AUG.

The flanking sequence comprises a sequence which corresponds to the target gene or sequence. That is, the flanking sequence comprises all or a part of the sense strand of the target molecule and can be RNA or DNA. By sense sequence is intended a sequence capable of hybridizing to the antisense portion capable of hybridizing to messenger RNA expressed by the target when the target is a gene, or to a target RNA or DNA molecule.

The flanking sequence may vary in length. It is recognized that the length may vary depending on the length and abundance of the target gene, and the specificity and affinity of the antisense portion for the target. While the length of the flanking sequence may vary, generally a length of about 10 to about 200 nucleotides, preferably about 20 to about 150 nucleotides, more preferably about 40 to about 100 nucleotides can be used.

The flanking sequence can be a naturally occurring or synthetic sequence. Where the sequence is synthetic, mismatch nucleotides can be incorporated into the structure to facilitate thermodynamic displacement of the antisense molecule by the target molecule. It is recognized that if the translation initiation site is inserted within the flanking sequence, this sequence insertion will provide nonhybridizing sequences and add to the decrease in homology between the flanking sequence and the antisense oligonucleotide. While it is recognized that a homology of up to 100% can be compatible with the intended displacement of the antisense strand from the flanking sequence, generally a homology of less than 90% is intended, preferably about 75% homology, more preferably about 65% homology.

A 7-methyl guanine (7 MeG) cap is known to increase the efficiency of translation. Thus, such a 7-methyl guanine cap can be included on the 5' end of the flanking sequence. See, for example, Shatkin, A. J. (1976) *Cell*, 9:645–653; Malone et al. (1989) *Proc. Natl. Acad. Sci. USA*, 86:6077–6081; Fuerst and Moss (1989) *J. Mol. Biol.*, 206:333–348 and Kozak, Marilyn (1991) *Gene Expression*, 1:117–125.

The antisense sequence of the expression cassette of the invention is constructed to hybridize with a nucleotide sequence of interest. Such nucleotide sequences of interest include messenger RNAs from target genes, viral RNAs or DNAs, and the like. The antisense strand is constructed to be homologous to the target. Generally, such homology will be greater than the homology exhibited by the antisense strand to the flanking sequence. Thus, in the presence of the target molecule, the antisense strand is displaced from the flanking sequence of the cassette and hybridizes with the target molecule. To enhance displacement, the cassette can be constructed such that the antisense sequence is longer than the flanking sequence, allowing for a 3' or 5' nonpaired overhang or "sticky end" to bind the target molecule. This sticky end will enhance displacement of the antisense oligonucleotide.

As discussed, the target molecule may vary. For treatment of malignant or neoplastic cell growth, the target molecule will correspond to a nucleotide which is only expressed or present in the neoplastic cell. In this case, the sequence of interest of the expression cassette will encode a toxin protein which is expressed in the presence of the target to kill the cell. The expression cassette could also encode a cytokine or interferon to fight neoplastic growth. In some instances, a combination of expression cassettes encoding different proteins may be provided. The target molecule can be a gene. Numerous target genes are known in the art. Such genes include c-myc, n-myc, c-myb c-abl, c-kit, c-mos, bcr-abl, bcl-2, retinoblastoma-l, p-53, GM-CSF, G-CSF, Ick, IGF-l, egr-I (A. Krieg, *ImmunoMethods* 1, 191 (1992)); c-fes (S. Ferrari et al., *Cell Growth Differ.* 1, 543 (1990)); c-fms (J. Wu et al., Oncogene 5, 873 (1990)); c-fos (A. Block et al., in (77). pp. 63–70); N-ras (T. Skorski et al., *J. Exp. Med.* 175, 743 (1992)); Ha-ras (T. Saison-Behmoaras et al., *EMBO J. MD.*, 111 (1991)); B-myb (M. Arsura et al., *Blood* 79, 2708 (1992)); CSF-1 (M. Birchenall-Roberts et al., *J. Immunol.* 145, 3290 (1990)); Myeloblastin (D. Bories et al., *Cell* 59, 959 (1988)); Erythropoietin (O. Hermine et al., *Blood* 78, 2253 (1991)); MZF-I (L. Bavisotto et al., *J Exp. Med.* 174, 1097 (1991)); mdrl (L. Rivoltini et al., *Int. J Cancer* 46, 727 (1990)); IGF-I receptor (P. Porcu et al., *Mol. Cell. Biol.* 12, 5069 (1992)); Growth hormone (D. Weingent, J. Blalock, R. LeBoeuff, *Endocrinology* 128, 2053 (1991)); EGR-1 (L. Neyses, J. Nouskas, H. Vetter, *Biochem. Biophys. Res. Commun.* 181, 22 (1991)); G proteins (Supra (1992)); MHC-1# (M. Cambe et al., *Anti-Cancer Drug Des.* 7, 341 (1992)); Angiotensinogen (J. Cook et al., *Antisense Res. Dev.* 2, 199 k$^{1992}$); Myogenin (A. Brunetti et al., *J. Biol*

*Chem.* 265, 13435 (1990)); LH receptor** (A. West and B. Cooke, *Mol. Cell Endocrinol.* 79, R9 (1991)); Cellular retinol-binding protein I F. Cope, J. Wille, L. D. Tomei, in (77), pp. 125-142; TNF-α (A. Witsell and L. Schook, *Proc. Natl. Acad. Sci. U.S.A.* 89, 4754 (1992)).

Target molecules include but are not limited to the CD4 gene, see, Accession No. X87579; CFTR gene (Varon et al. (1995) *Hum. Mol. Genet* 4:1463–1464); human C3d/ Epstein-Barr virus receptor (Fujisaku et al. (1989) *J. Biol. Chem.* 264:2118–2125); Human MHC class I CD8 alpha-chain gene (Accession M27161, Nakayama et al. (1989) *Immunogenetics* 30:393–397); human elastase 2 mRNA (Accession M16631), Fletcher et al. (1987) *Biochemistry* 26:7256–7261); Human elastin mRNA (Accession M36860, Fazio et al. (1988) *J. Invest. Dermatol.* 91:458–464); human intercellular adhesion molecule 1 gene (Accession U86814); human interleukin 1-beta converting enzyme isoform beta mRNA (Accession U13697 Alnemri et al. (1998) *J Biol. Chem.* 270:4312–4317); human immunoglobulin C mu-C delta locus (Accession X57331, Word et al. (1989) *Int. Immunol* 1:296–309); human interleukin 2 gene (Accession J00264, Maeda et al. (1983) *Biochem. Biophys. Res. Commun.* 115:1040–1047; Fujita et al. (1983) *Proc. Natl. Acad. Sci. USA* 80:7437–7441); human MHC Class I antigen HLA-B (Accession U88407); human MHC class II HLA-DPA1 antigen (Accession U87556); etc. herein incorporated by reference.

Likewise, the target molecule may be a RNA or DNA from a virus. In this manner, viral replication and growth can be inhibited. Such viral genes include but are not limited to sequences from Coxsackievirus (Marquardt and Ohlinger (1995) *J. Virol. Methods* 53:189–199); Dengue virus, see Accession No. U88535; encephalitis virus, see, Accession No. AB001026; Ebola virus (Sanchez et al. (1989) *Virology* 170:81–91, Accession No. L11365); Epstein-Barr virus (Baer et al. (1984) *Nature* 310:207–211), Echovirus 32 (Huttunen et al. (1996) *J. Gen. Virol.* 77:715–725); Enterovirus (VP4-VP2 capsid 3D RNA polymerase genes Pulli et al. (1995) *Virology* 212:30–38); influenza A virus (Guan et al. (1996) *J. Virol.* 70:8041–8046); hepatitis B virus (Fukuda et al. (1995) *J. Infect. Dis.* 172:1191–1197); hepatitis C virus (Hitomi et al. (1995) *Viral Immunol.* 8:109–119); hepatitis D virus (Khudyakov et al. (1993) *Virus Res.* 27:13–24); hepatitis E virus (Tam et al. (1990) *Science* 247:1335–1449, Accession No. M32400); hepatitis G virus (Accession No. U86023); HIV (Accession U04908, Gao et al. (1996) *J. Virol.* 70:1651–1667); human papillomavirus (Accession U37537, Wu et al. (1993) *Lancet* 341:522–524); influenza A virus (Accession U86987); human rhinovirus (Accession D00239, Hughes et al. (1988) *J. Gen. Virol.* 69:49–58); Sendai virus (Accession D00053 N00053, Morgan and Rakestraw (1986) *Virology* 154:31–40); gastroenteritis virus TFI virion protein (gene (Accession Z35758; Chen et al. (1995) *Virus Res.* 38:83–89); herpes simplex type 2 virus (Accession Z86099, McGeoch et al. (1987) *J. Gen Virol.* 68:19–38); Venezuelan equine encephalitis virus (Accession L01442, Kinney et al. (1986) *Virology* 152:400–413); herein incorporated by reference.

Other genes of interest include, for example, jun, bFGF, wnt-1, TGF-beta, spi-1 for cytomegalovirus; NDR, c-erbB-2 for herpes simplex virus, types 1 and 2; bcl-2 and bci-abl for human papilloma virus; p53 and c-myb for hepatitis, type B; 1-myc and ras for influenza virus; etc.

Methods are generally available in the art for construction of the masked expression cassettes. See, for example, Sambrook et al., Cold Spring Harbor, N.Y. RNA/DNA molecules as well as antisense oligonucleotides can be made in accordance with known techniques. See, e.g., U.S. Pat. No. 5,149,797; 5,175,273; Uhlmann and Peyman (1990) *Chem. Rev.*, 90:543–584 and the references cited therein. The antisense oligonucleotides, which may be deoxyribonucleotide or ribonucleotide sequences which are capable of complementary binding to the target molecule. Such antisense oligonucleotides may be oligonucleotides wherein at least one, or all, of the internucleotide bridging phosphate residues are modified phosphates, such as methyl phosphonates, methyl phosphonothioates, phosphoromorpholidates, phosphoropiperazidates and phosphoramidates. For example, some, for example, every other one, of the internucleotide bridging phosphate residues may be modified as described. In another example, such antisense oligonucleotides are oligonucleotides wherein at least one, or all, of the nucleotides contain a 2' loweralkyl moiety (e.g., C1–C4, linear or branched, saturated or unsaturated alkyl, such as methyl, ethyl, ethenyl, propyl, 1-propenyl, 2-propenyl, and isopropyl). See also Furdon et al. (1989) *Nucleic Acids Res.*, 17:9193–9204; Agrawal et al. (1990) *Proc. Natl. Acad. Sci. USA*, 87:1401–1405; Baker et al. (1990) *Nucleic Acids Res.*, 18:3537–3543; Sproat et al. (1989) *Nucleic Acids Res.*, 17:3373–3389; Walder and Walder (1988) *Proc. Natl. Acad. Sci. USA*, 85:5011–5015.

Modification of the phosphodiester backbone has been shown to impart stability and may allow for enhanced affinity and increased cellular penetration of ODNs. Additionally, chemical strategies may be employed to replace the entire phosphodiester backbone with novel linkages. Phosphorothioate and methylphosphonate modified ODNs may be made through automated ODN synthesis.

A phosphorodithioate version of the phosphorothioate can be synthesized. In the dithioate linkage, the non-bridging oxygens can be substituted with sulfur. This linkage is highly nuclease resistant.

Sugar modifications may also be used to enhance stability and affinity of the molecules. The alpha-anomer of a 2'-deoxyribose sugar has the base inverted with respect to the natural beta-anomer. ODNs containing alpha-anomer sugars are resistant to nuclease degradation.

If necessary, targeted cassette can be modified to increase stability in vivo. Thus, nuclease-resistant oligonucleotides can be utilized, such as PS and MP oligonucleotides. See, for example, Miller, P. (1991) *Biotechnology,* 9:358 and Stein et al. (1991) *Pharmacol. Ther.,* 52:365.

The targeted expression cassettes of the invention can be synthesized easily and in bulk. The development of phosphoramidite chemistry and its elaboration into an automated technology have greatly enhanced the ease with which oligos are synthesized and consequently their availability. See, for example, Beaucage and Caruthers (1981) *Tetrahedron Lett.,* 37:3557 and Zon and Geiser (1991) *Anti-Cancer Drug Des.,* 6:539.

The methods, oligonucleotides and formulations of the present invention have a variety of uses. They are useful in preventing the proliferation and growth of neoplastic cells. The methods, oligonucleotides and compositions of the present invention are also useful as therapeutic agents in the treatment of disease. They also find use in fermentation processes where it is desirable to have a means for regulating the expression of a gene to be expressed at a certain time or any instance where it is desirable to regulate gene expression.

The term "antisense oligonucleotides" includes the physiologically and pharmaceutically acceptable salts thereof: i.e., salts that retain the desired biological activity of the parent compound and do not impart undesired toxicological effects thereto. Examples of such salts are (a) salts formed with cations such as sodium, potassium, spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, napthalenesulfonic acid, methanesulfonic acid, p-toluenesulfonic acid, napthalenedisulfonic acid, polygalacturonic acid, and the like; and (d) salts formed from elemental anions such as chlorine, bromine, and iodine.

Formulations of the present invention comprise the masked cassette in a physiologically or pharmaceutically acceptable carrier, such as an aqueous carrier. Thus, formulations for use in the present invention include, but are not limited to, those suitable for parenteral administration, including subcutaneous, intradermal, intramuscular, intravenous and intraarterial administration, as well as topical administration (i.e., administration of an aerosolized formulation of respirable particles to the lungs of a patient afflicted with cystic fibrosis). The formulations may conveniently be presented in unit dosage form and may be prepared by any of the methods well known in the art. Such formulations are described in, for example, *Remington's Pharmaceutical Sciences* 19th ed., Osol, A. (ed.), Mack Easton Pa. (1980). The most suitable route of administration in any given case may depend upon the subject, the nature and severity of the condition being treated, and the particular active compound which is being used.

The present invention provides for the use of the targeted masked cassette having the characteristics set forth above for the preparation of a medicament for the various disorders. In the manufacture of a medicament according to the invention, the masked cassette is typically admixed with, inter alia, an acceptable carrier. The carrier must, of course, be acceptable in the sense of being compatible with any other ingredients in the formulation and must not be deleterious to the patient. The carrier may be a solid or a liquid. One or more antisense oligonucleotides may be incorporated in the formulations of the invention, which may be prepared by any of the well known techniques of pharmacy consisting essentially of admixing the components, optionally including one or more accessory therapeutic ingredients.

Formulations of the present invention may comprise sterile aqueous and non-aqueous injection solutions of the active compound, which preparations are preferably isotonic with the blood of intended recipient and essentially pyrogen free. These preparations may contain anti-oxidants buffers, bacteriostats and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use.

In the formulation the targeted cassette may be contained within a lipid particle or vesicle, such as a liposome or microcrystal, which may be suitable for parenteral administration. The particles may be of any suitable structure, such as unilamellar or plurilamellar, so long as the targeted cassette is contained therein. Positively charged lipids such as N-[1-(2,3-diolcoyloxi)propyl]-N,N,N-trimethyl-amoniummethylsulfate, or "DOTAP," are particularly preferred for such particles and vesicles. The preparation of such lipid particles is well known. See, e.g., U.S. Pat. Nos. 4,880,635 to Janoff et al.; 4,906,477 to Kurono et al.; 4,911,928 to Wallach; 4,917,951 to Wallach; 4,920,016 to Allen et al.; 4,921,757 to Wheatley et al.; etc.

The dosage of the targeted cassette administered will depend upon the particular method being carried out, and when it is being administered to a subject, will depend on the disease, the condition of the subject, the particular formulation, the route of administration, etc. In general, intracellular concentrations of the cassette of from 0.05 to 50 $\mu$M, or more particularly 0.2 to 5 $\mu$M, are desired. For administration to a subject such as a human, a dosage of from about 0.01 .1, or 1 mg/Kg up to 50, 100, or 150 mg/Kg is employed.

Current technology has focused on antisense molecules only. Antisense oligonucleotides bind the offending RNA molecules in the cell. To be effective, a high dosage of antisense molecules have to be delivered to each cell. The present invention provides for an effector molecule which increases the potency of antisense technology. In this manner, the cell can be manipulated more easily and a far lower dosage, potentially even a 1 molecule to 1 cell ratio can be effective.

It is the idea of specificity that provides the underlying feature of the present invention. Standard cytotoxic chemotherapy for conditions such as neoplastic disease is fraught with systemic toxicity. The ratio of the toxic dose to the therapeutic dose is relatively low, which reflects the large number of cellular targets affected by the chemotherapeutic agent and the agents inability to distinguish between normal and diseased cells. In theory, this problem is solved by taking advantage of the specificity conferred by Watson-Crick base pair formation by identifying an appropriate target.

The following experiments arc offered by way of illustration and not by way of limitation.

Experimental

Use of Targeted Cassette to Kill Neoplastic Cells

Following the protocols as essentially described above, a targeted cassette is constructed wherein the first strand has an RNA coding for toxin A. The toxin RNA is linked with upstream DNA sequences coding the sense portion of the p53 DNA sequence. The p53 protein is found in numerous cancer cells. Inserted within the p53 molecule is a Kozak sequence. An antisense structure is constructed which corresponds to the p53 sense nucleotide.

The targeted cassettes are provided to a patient in a pharmaceutically acceptable solution at a concentration of from about 0.01, .1, or 1 mg/Kg up to 50, 100, or 150 mg/Kg.

Use of Targeted Cassette as Antiviral Drug

FIG. 1 depicts utilization of the masked targeted expression cassette as an antiviral agent (Black RNA Drug). Features of the cassette are identified by the provided key. The sense strand has a 7 meG cap at its 5' end. In the inactive form, the antisense strand is hybridized to the flanking sequences of the sense strand; such that the Kozak sequence is masked. Mismatch area between the Kozak sequence and the antisense strand is indicated by lack of hydrogen bonding. Upon presentation of active viral RNA which has perfect homology to the antisense strand, the antisense strand dissociates from the sense strand and binds the viral RNA, which renders the viral RNA inactive. Furthermore, upon dissociation of the antisense strand, the Kozak sequence is unmasked and translation of the toxin protein commences from the AUG initiation codon. Upon production of toxic quantities of mature toxin, the cell hosting the virus is destroyed.

Targeted Cassette with Totally Complementary Antisense and Flank Sequences

Figure 2:
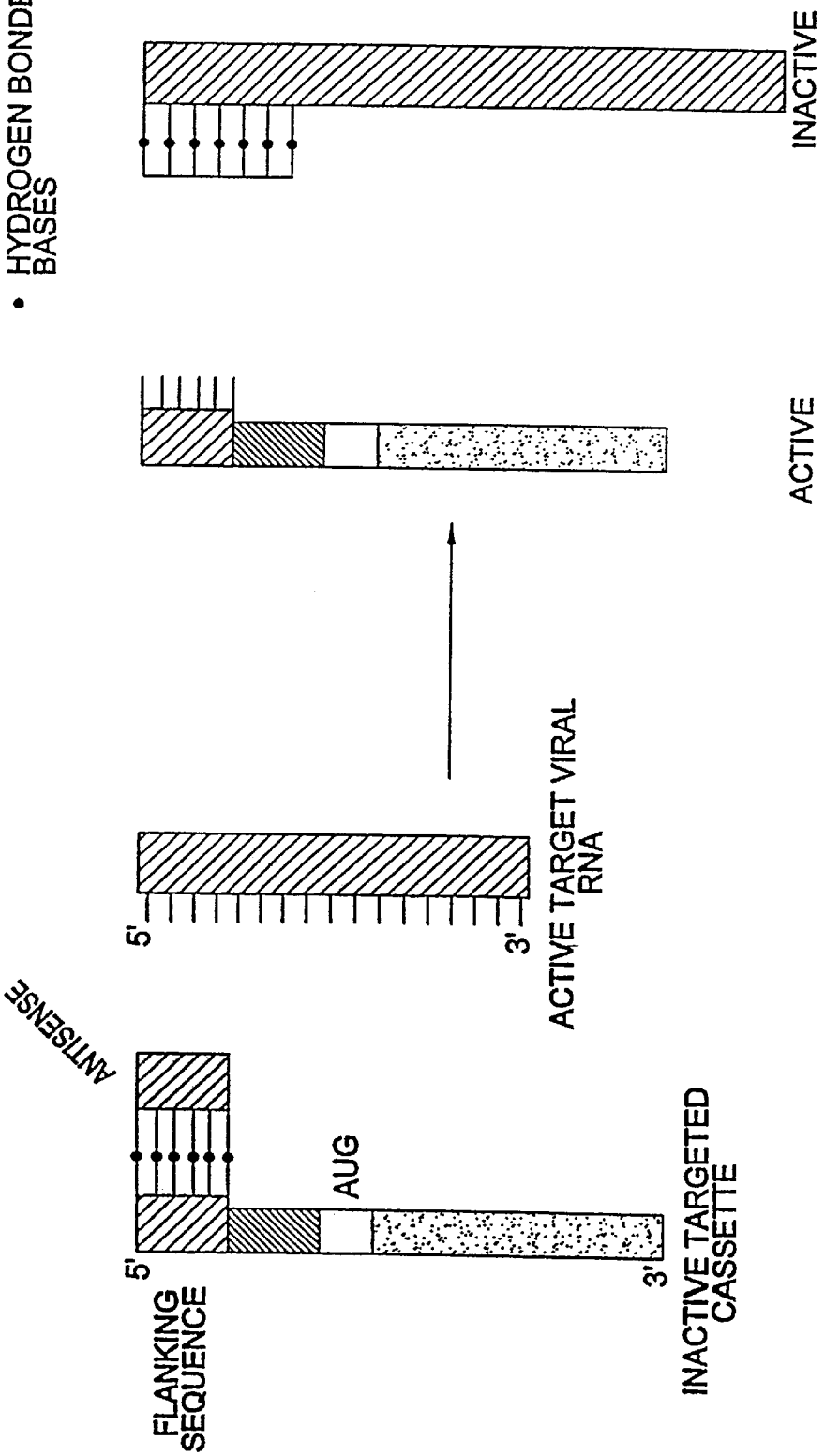
FIG. 2 provides a diagrammatic sketch of the masked targeted expression cassette in which the target sequence of the sense strand is completely complementary to the antisense strand.

FIG. 2 depicts a masked targeted expression cassette in which the viral target sequence of the sense strand is completely complementary to the antisense strand. In the inactive targeted cassette, ribosomal assembly and scanning from the 5' end is prevented by the duplex between the antisense strand and the flanking sequence. In this example, displacement of the antisense strand and activation of expression of the gene of interest (lac Z) can be tested by assaying for β-galactosidase activity.

Targeted Cassette with Increased Target Specificity

Figure 3:
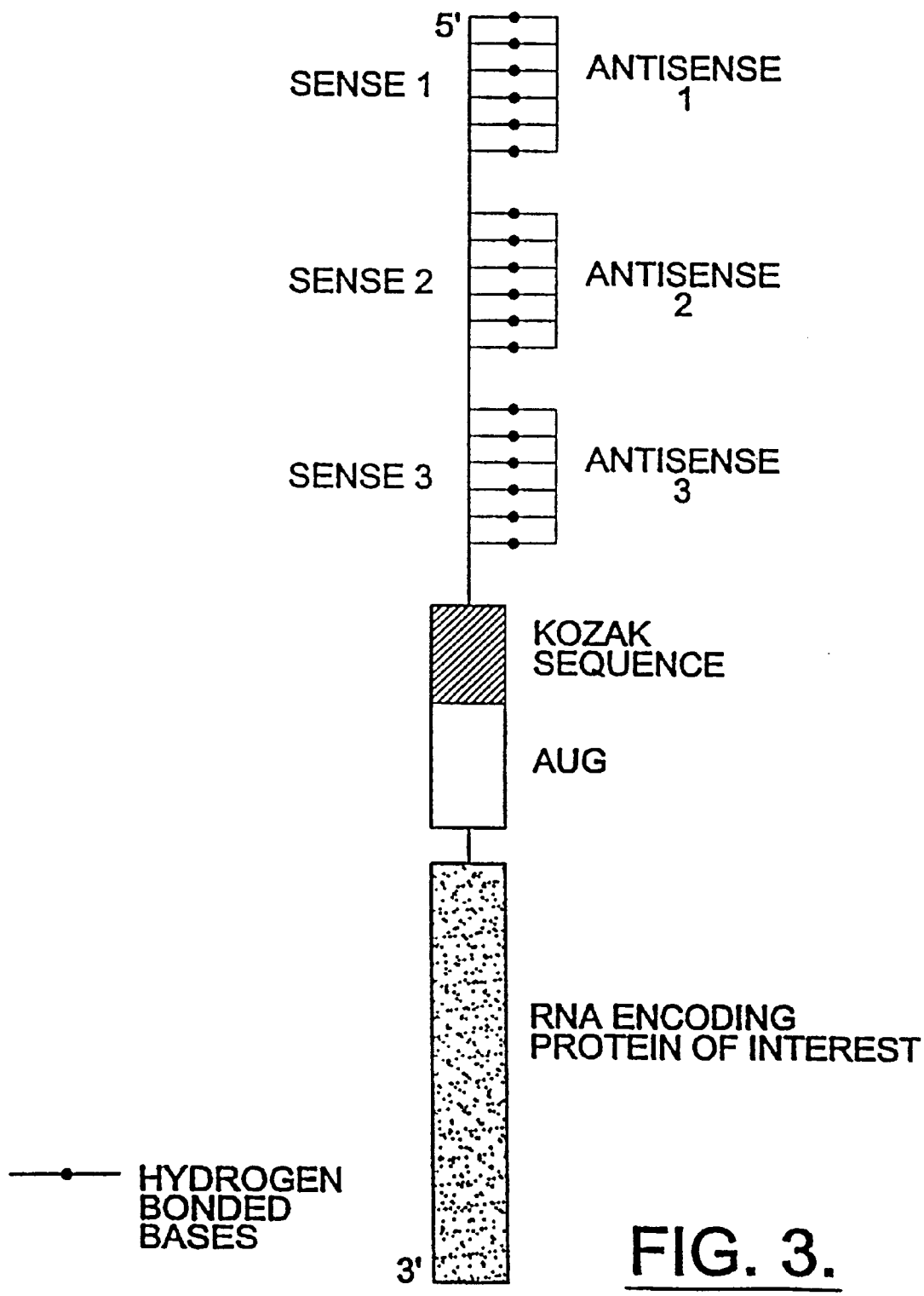
FIG. 3 provides a diagrammatic sketch of the masked expression cassette with concatenated geometry for increasing target specificity.
Figure 4:
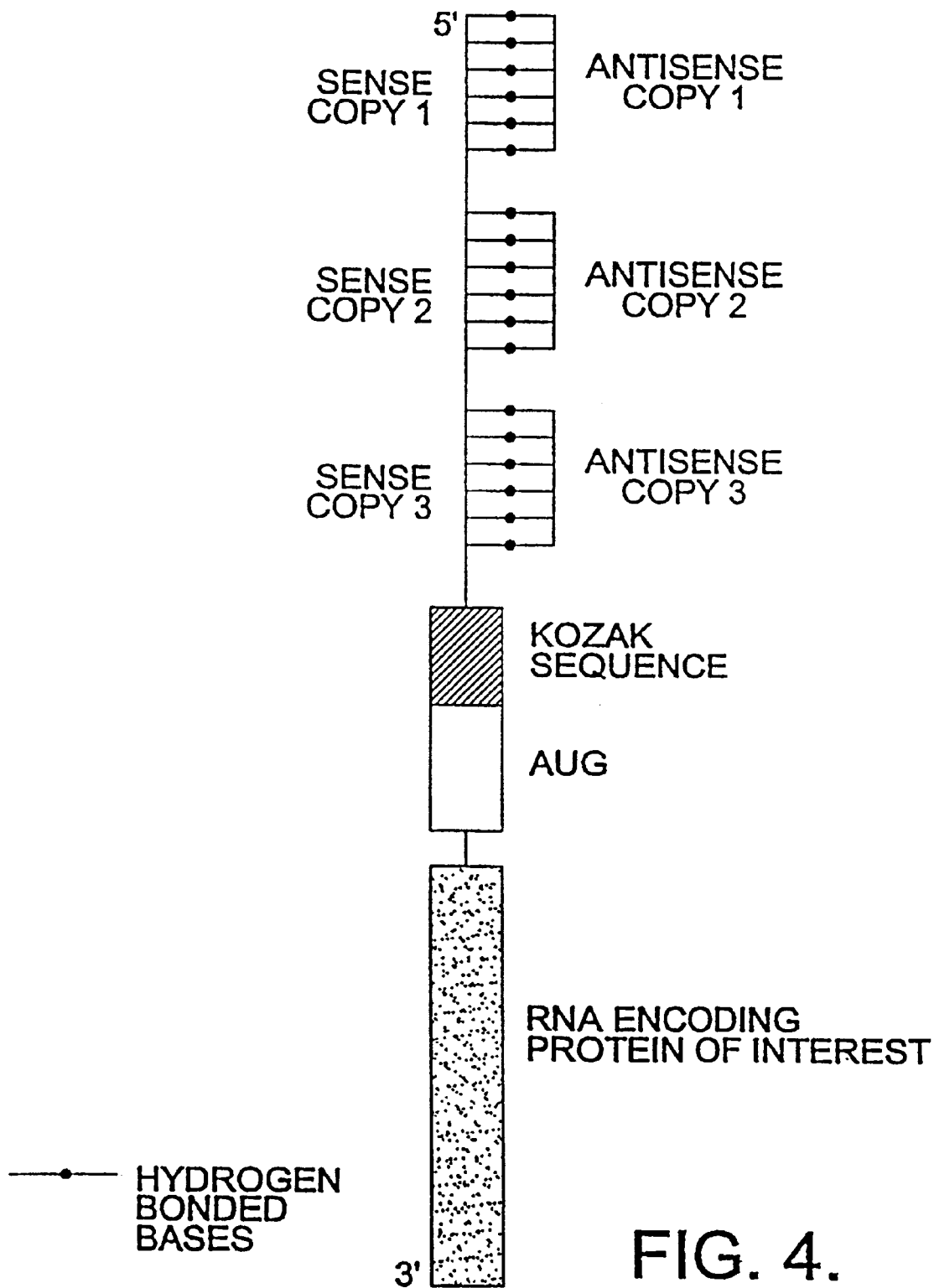
FIG. 4 provides a diagrammatic sketch of the masked targeted expression cassette with concatenated geometry which requires a quantity threshold of target molecules for initiation of translation of the desired gene.
Figure 5:
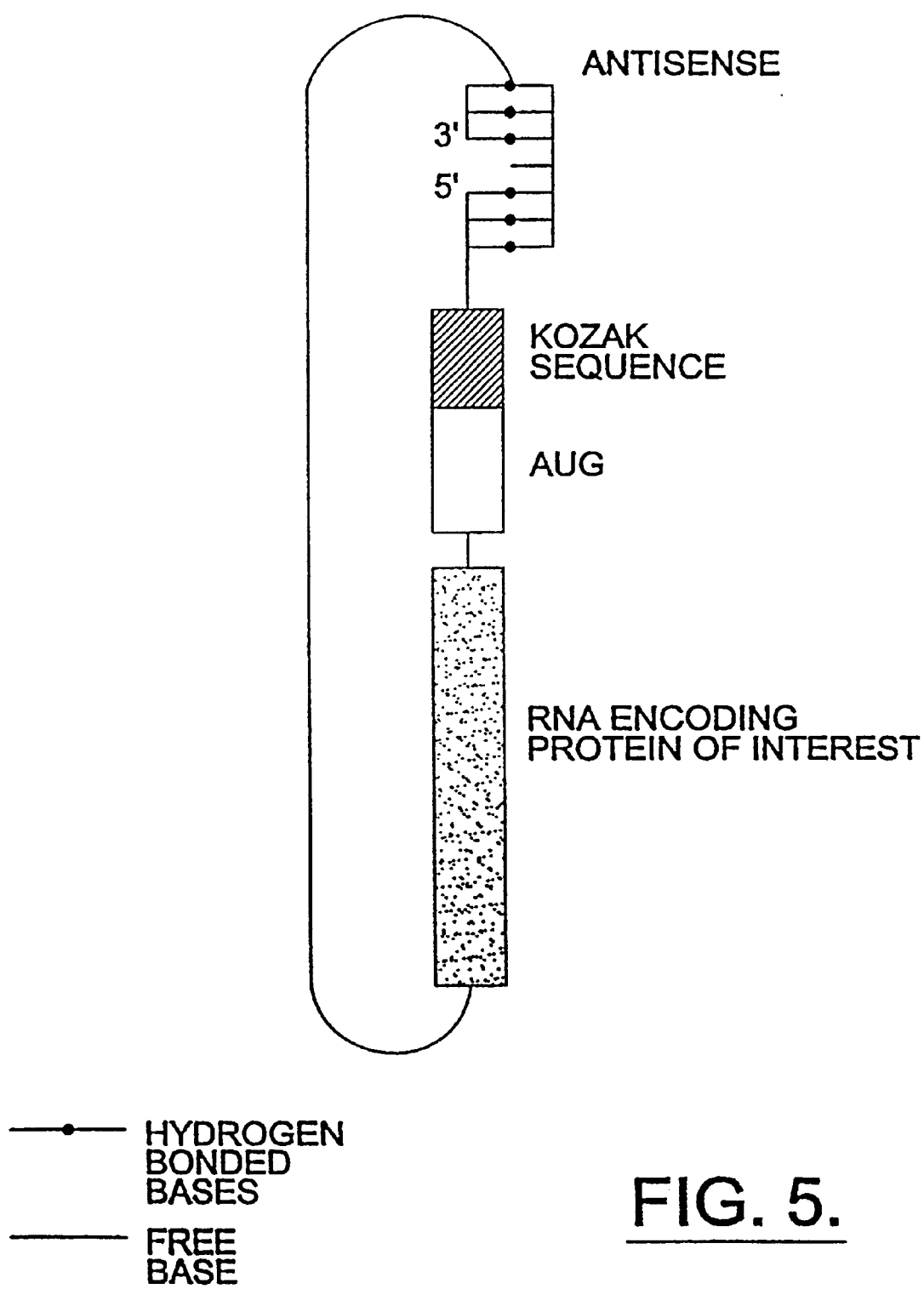
FIG. 5 provides a diagrammatic sketch of a circular masked targeted expression cassette for increased compactness and decreased viscosity.
Figure 6:
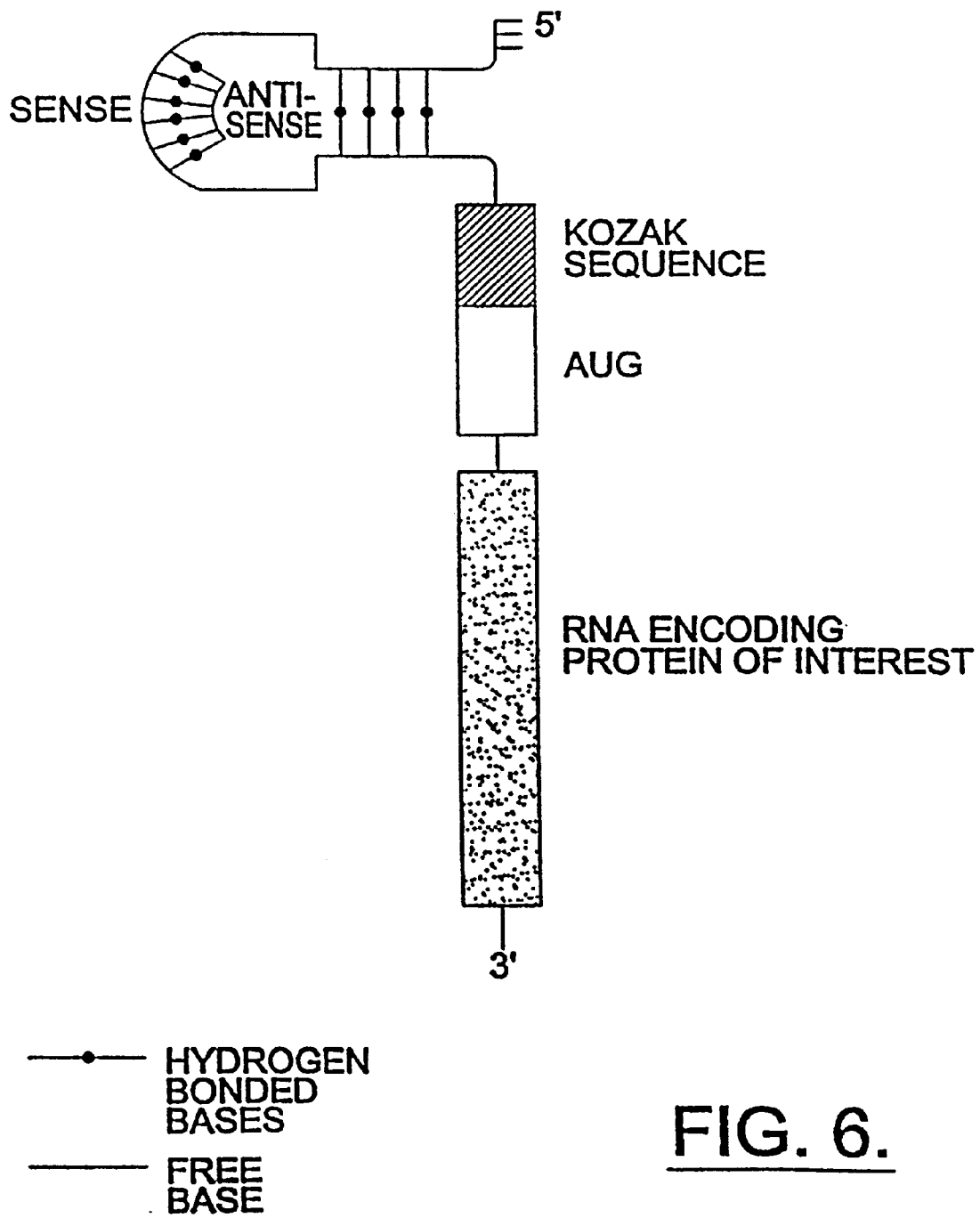
FIG. 6 provides a diagrammatic sketch of a stem-loop masked targeted expression system for increased compactness.
Figure 7:
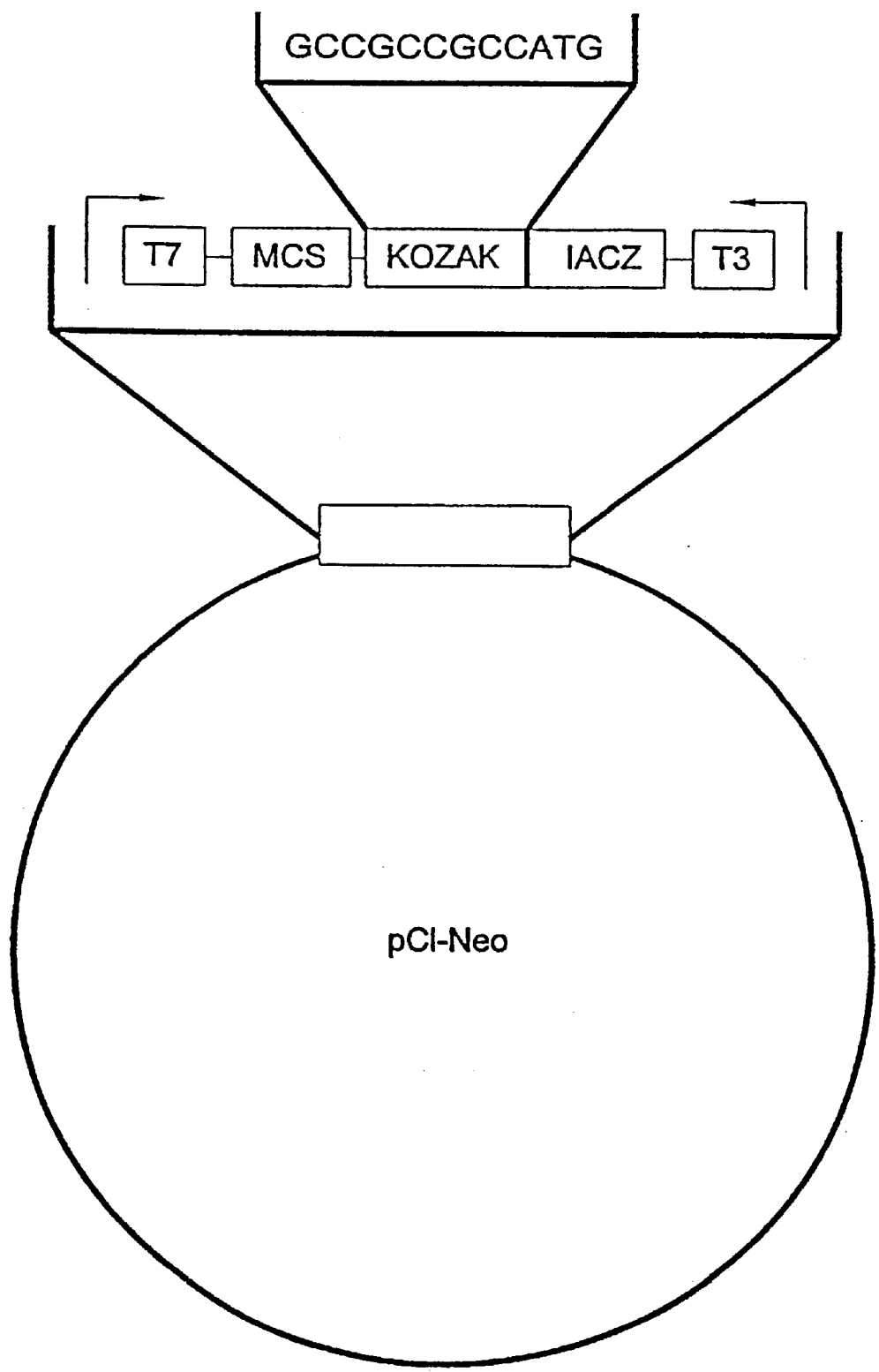
FIG. 7 provides an example of a construct for production of the sense strand of the targeted cassette. The Kozak sequence is also shown (SEQ ID NO: 17).
Figure 8:
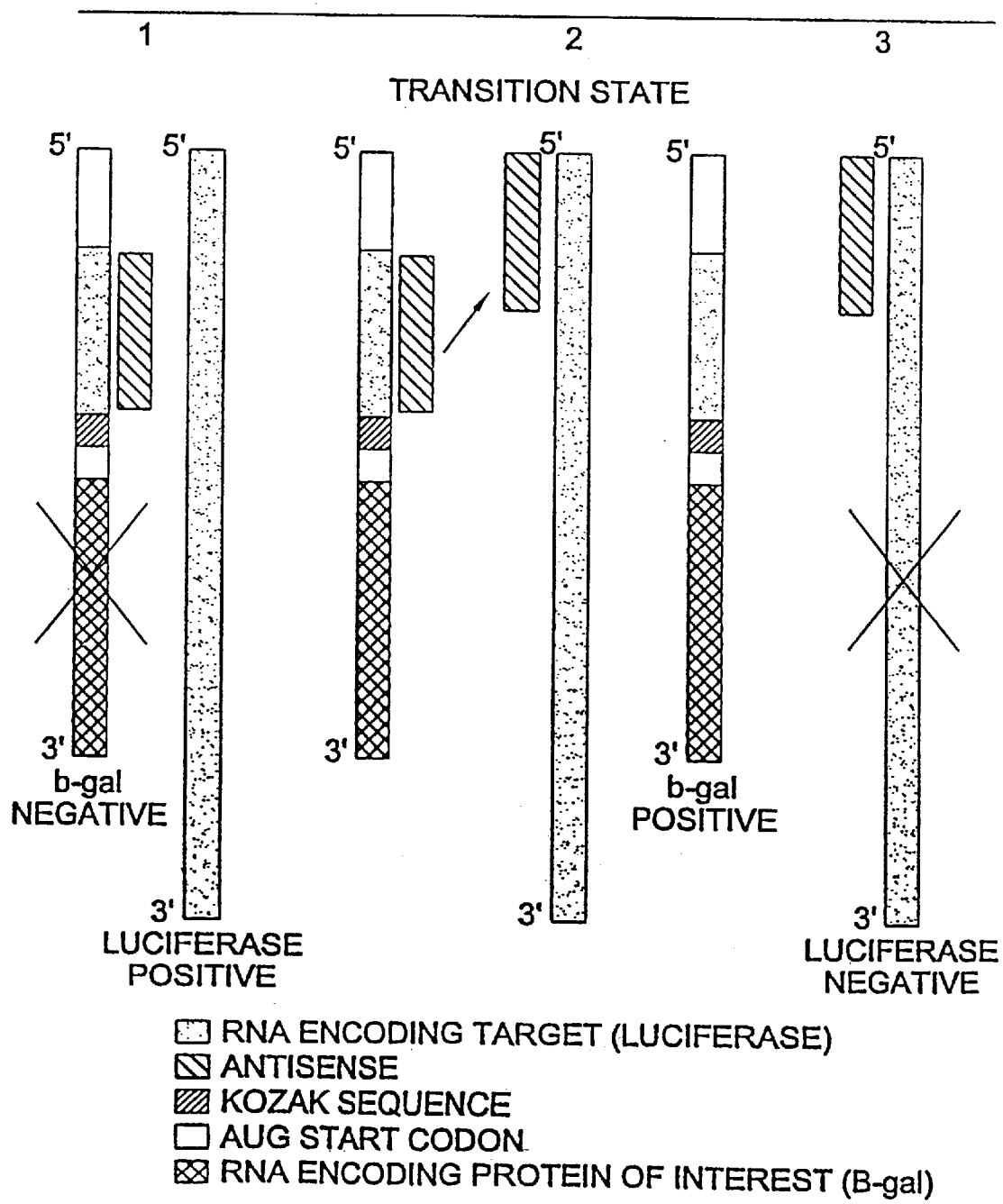
FIG. 8 provides a diagrammatic sketch of an in vitro experiment utilizing the masked targeted expression cassette.

FIG. 3 depicts a masked targeted expression cassette with concatenated geometry for increasing target specificity for initiation of translation of the gene of interest. Each antisense/sense combination (1–3)) corresponds to a different target sequence. For example, 1 corresponds to a viral RNA, 2 corresponds to a cytokine RNA, and 3. corresponds to a host specific protein. RNA encoding the protein of interest is only expressed when all 3 target sequences are present in the target cell, effecting displacement of all 3 antisense sequences from the sense sequences of the cassette, thereby allowing ribosomal assembly and scanning from the 5' end to proceed to the Kozak sequence and the AUG start codon.

Targeted Cassette with Target Quantity Threshold

FIG. 4 depicts a masked targeted expression cassette with concatenated geometry for requiring a target quantity threshold for initiation of translation. All sense/antisense combinations (1–3) correspond to the same target RNA. RNA encoding the protein of interest is only expressed when the target RNA is present in sufficient quantity (in this example 3 copies) in the target cell, effecting displacement of all 3 antisense sequences from the sense sequences of the cassette, thereby allowing ribosomal assembly and scanning from the 5' end to proceed to the Kozak sequence and the AUG start codon. The concatenated geometry thus requires a threshold quantity of the target RNA for initiation of translation. Such concatenated cassette constructs are particularly useful for targeting cancer cells with abnormally high number of copies of a particular mRNA. The constructs may also be made in combination with the constructs of FIG. 3.

Circular Targeted Cassette

FIG. 5 depicts a circular masked targeted expression cassette.

An antisense molecule complementary to a target molecule is bound to complementary sequences at the 3' and 5' end of the targeted expression cassette, thereby preventing ribosome assembly and scanning from the 5' end. Thus, displacement of the antisense strand in the presence of a complementary target molecule allows for translation and expression of the desired protein. The circular configuration may be more compact and less viscous, thereby having particularly desirable properties for drug delivery applications.

Stem-loop Targeted Cassette

FIG. 6 depicts a stem-loop masked targeted expression cassette. An antisense molecule complementary to a target molecule is bound to complementary sequences within the loop structure, further stabilizing the stem-loop structure. Ribosomal scanning from the 5' end is prevented from proceeding to the Kozak sequence and the initiation AUG codon by the stable secondary structure of the complex. Displacement of the antisense strand in the presence of a complementary target molecule provides a less stable stem-loop structure unable to prevent ribosomal scanning commenced from the 5' end.

FIG. 7: Armed Sense Strand Plasmid Construct.

FIG. 7 depicts a $_{P}$CI-Neo (Promega Corp.) plasmid construct for production of the sense RNA strand of a targeted expression cassette. The complete sequence of the depicted MCS-Kozak-lac Z is set forth in SEQ ID NO: 1. Alternative flanking sequences corresponding to portions of the firefly luciferase mRNA are inserted into the multiple cloning site (MCS), such that transcription from the $T_7$ promoter yields RNA comprising from the 5' end; luciferase segment-Kozak-βgal. The alternative luciferase sense segments are set forth in SEQ ID NO: 2, 3, 4, 5, 6, 7 or 8.

FIG. 8 In vitro determination of activity of masked targeted expression cassette.

Sense strand RNA of the masked targeted cassette is produced by in vitro transcription of the construct depicted in FIG. 7, by use of the Riboprobe® Combination System (Catalogue No. P1450, Promega Corp.).

Antisense sequences corresponding to portions of the target molecule (firefly luciferase RNA, Catalogue No. L4561, Promega Corp.) are hybridized to complementary flanking, sequences of the sense strand of the targeted cassette.

SEQ ID NO: 2, 3, 4, 5, 6, 7 or 8 list alternative flanking sequences and SEQ ID NO: 9, 10, 11, 12, 13, 14 or 15 list the corresponding antisense sequences, respectively. The full length firefly luciferase RNA, according to which the flanking sense sequences and corresponding antisense sequences are made is set forth in SEQ ID NO: 16. The hybridized mixture is introduced to an in vitro translation mixture containing ribosomes and full length firefly luciferase RNA (Flex®, Rabbit Reticulocyte Lysate System, Catalogue No. L4540, Promega Corp.). Control reactions will lack the masked cassette.

After completion of translation, the mixture will be assayed for β-galactosidase (β-gal) and luciferase activities. Negative luciferase and positive β-gal activity indicates successful inhibition of the target molecule and successful expression of the gene of interest.

The diagram depicts the mechanism of the assay. In panel 1, the antisense sequence is bound to complementary flanking sequence of the targeted cassette. Ribosomal scanning commenced from the 5' end is blocked by the antisense/sense duplex, thereby preventing translation of the β-gal RNA. Displacement and binding of the antisense to target luciferase RNA (panel 2) has a two-fold effect (panel 3). β-gal can be expressed from the unmasked cassette (β-gal positive) and expression of the target is blocked by binding of the antisense to the target (luciferase negative).

Other modifications and embodiments of the invention will come to mind in one skilled in the art to which this invention pertains having the benefit of the teachings presented herein. Therefore, it is to be understood that the invention is not to be limited to the specific embodiments disclosed. Although specific terms are employed, they are used in generic and descriptive sense only and not for purposes of limitation, and that modifications and embodiments are intended to be included within the scope of the appended claims.

What is claimed is:

1. A masked expression cassette comprising a first strand comprising an RNA sequence which encodes a protein of interest wherein the RNA sequence is linked downstream of a flanking sequence and a translation initiation site operably linked upstream of the RNA sequence: and, a second strand bound to the flanking sequence, wherein the second strand comprises an antisense sequence corresponding to the flanking sequence and a target nucleic acid sequence, where when the masked expression cassette is contacted with the target nucleic acid the second strand dissociates from the cassette allowing expression of the protein of interest.

2. The cassette of claim 1, wherein said cassette further comprises a 7-methyl guanine cap linked to the 5' end of the flanking sequence.

3. The cassette of claim 1, wherein said protein of interest is a toxin.

4. The cassette of claim 1, wherein said target is unique to neoplastic cells.

* * * * *

SEQUENCE LISTING

<160> NUMBER OF SEQ ID NOS: 19

<210> SEQ ID NO 1
<211> LENGTH: 4279
<212> TYPE: DNA
<213> ORGANISM: Artificial Sequence
<220> FEATURE:
<223> OTHER INFORMATION: Recombinant Molecule containing multiple
      cloning site, kozak sequence, LacZ gene.
<221> NAME/KEY: misc_feature
<222> LOCATION: (1)...(64)
<223> OTHER INFORMATION: Multiple cloning site
<221> NAME/KEY: misc_feature
<222> LOCATION: (65)...(79)
<223> OTHER INFORMATION: Consensus sequence for the "Kozak sequence"
      (translation initiation)
<221> NAME/KEY: prim_transcript
<222> LOCATION: (80)...(4279)
<223> OTHER INFORMATION: Beta galactosidase

<400> SEQUENCE: 1

```
ttaatacgac tcactatagg ctagcctcga gaattcacgc gtggtacctc tagagtcgac       60
ccgggccgcc gccaccatgg cgcagcacca tggcctgaaa taacctctga agaggaact      120 tggttaggta ccttctgagg cggaaagaac cagctgtgga atgtgtgtca gttagggtgt     180
ggaaagtccc caggctcccc agcaggcaga agtatgcaaa gcatgcatct caattagtca     240
gcaaccaggt gtggaaagtc cccaggctcc ccagcaggca gaagtatgca aagcatgcat     300
ctcaattagt cagcaaccat agtcccgccc ctaactccgc ccatcccgcc cctaactccg     360
cccagttccg cccattctcc gccccatggc tgactaattt tttttattta tgcagaggcc     420
gaggccgcct cggcctctga gctattccag aagtagtgag gaggcttttt tggaggccta     480
ggcttttgca aaaagcttgg gatctctata atctcgcgca acctattttc ccctcgaaca     540 cttttaagc cgtagataaa caggctggga cacttcacat gagcgaaaaa tacatcgtca     600
cctgggacat gttgcagatc catgcacgta aactcgcaag ccgactgatg ccttctgaac     660
aatggaaagg cattattgcc gtaagccgtg gcggtctggt accggtgggt gaagaccaga     720
aacagcacct cgaactgagc gcgatattg cccagcgttt caacgcgctg tatggcgaga     780
tcgatcccgt cgttttacaa cgtcgtgact gggaaaaccc tggcgttacc caacttaatc     840
gccttgcagc acatccccct ttcgccagct ggcgtaatag cgaagaggcc cgcaccgatc     900
gcccttccca acagttgcgc agcctgaatg gcgaatggcg ctttgcctgg tttccggcac     960
cagaagcggt gccggaaagc tggctggagt gcgatcttcc tgaggccgat actgtcgtcg    1020 tccctcaaa ctggcagatg cacggttacg atgcgcccat ctacaccaac gtaacctatc    1080
ccattacggt caatccgccg tttgttccca cggagaatcc gacgggttgt tactcgctca    1140
catttaatgt tgatgaaagc tggctacagg aaggccagac gcgaattatt tttgatggcg    1200
ttaactcggc gtttcatctg tggtgcaacg ggcgctgggt cggttacggc caggacagtc    1260
gtttgccgtc tgaatttgac ctgagcgcat ttttacgcgc cggagaaaac cgcctcgcgg    1320
tgatggtgct gcgttggagt gacggcagtt atctggaaga tcaggatatg tggcggatga    1380
gcggcatttt ccgtgacgtc tcgttgctgc ataaaccgac tacacaaatc agcgatttcc    1440
atgttgccac tcgctttaat gatgatttca gccgcgctgt actggaggct gaagttcaga    1500
tgtgcggcga gttgcgtgac tacctacggg taacagtttc tttatggcag ggtgaaacgc    1560
aggtcgccag cggcaccgcg cctttcggcg gtgaaattat cgatgagcgt ggtggttatg    1620
```

-continued

```
ccgatcgcgt cacactacgt ctgaacgtcg aaaacccgaa actgtggagc gccgaaatcc    1680
cgaatctcta tcgtgcggtg gttgaactgc acaccgccga cggcacgctg attgaagcag    1740
aagcctgcga tgtcggtttc cgcgaggtgc ggattgaaaa tggtctgctg ctgctgaacg    1800
gcaagccgtt gctgattcga ggcgttaacc gtcacgagca tcatcctctg catggtcagg    1860
tcatggatga gcagacgatg gtgcaggata tcctgctgat gaagcagaac aactttaacg    1920
ccgtgcgctg ttcgcattat ccgaaccatc cgctgtggta cacgctgtgc gaccgctacg    1980
gcctgtatgt ggtggatgaa gccaatattg aaacccacgg catggtgcca atgaatcgtc    2040
tgaccgatga tccgcgctgg ctaccggcga tgagcgaacg cgtaacgcga atggtgcagc    2100
gcgatcgtaa tcacccgagt gtgatcatct ggtcgctggg gaatgaatca ggccacggcg    2160
ctaatcacga cgcgctgtat cgctggatca aatctgtcga tccttcccgc ccggtgcagt    2220
atgaaggcgg cggagccgac accacggcca ccgatattat ttgcccgatg tacgcgcgcg    2280
tggatgaaga ccagcccttc ccggctgtgc cgaaatggtc catcaaaaaa tggctttcgc    2340
tacctggaga gacgcgcccg ctgatccttt gcgaatacgc ccacgcgatg ggtaacagtc    2400
ttggcggttt cgctaaatac tggcaggcgt ttcgtcagta tccccgtttta cagggcggct    2460 tcgtctggga ctgggtggat cagtcgctga ttaaatatga tgaaaacggc aacccgtggt    2520
cggcttacgg cggtgatttt ggcgatacgc cgaacgatcg ccagttctgt atgaacggtc    2580
tggtctttgc cgaccgcacg ccgcatccag cgctgacgga agcaaaacac cagcagcagt    2640
ttttccagtt ccgtttatcc gggcaaaacca tcgaagtgac cagcgaatac ctgttccgtc    2700
atagcgataa cgagctcctg cactggatgg tggcgctgga tggtaagccg ctggcaagcg    2760
gtgaagtgcc tctggatgtc gctccacaag gtaaacagtt gattgaactg cctgaactac    2820
cgcagccgga gagcgccggg caactctggc tcacagtacg cgtagtgcaa ccgaacgcga    2880
ccgcatggtc agaagccggg cacatcagcg cctggcagca gtggcgtctg gcggaaaacc    2940
tcagtgtgac gctccccgcc gcgtcccacg ccatcccgca tctgaccacc agcgaaatgg    3000
atttttgcat cgagctgggt aataagcgtt ggcaatttaa ccgccagtca ggctttctttt   3060 cacagatgtg gattggcgat aaaaaacaac tgctgacgcc gctgcgcgat cagttcaccc    3120
gtgcaccgct ggataacgac attggcgtaa gtgaagcgac ccgcattgac cctaacgcct    3180
gggtcgaacg ctggaaggcg gcgggccatt accaggccga agcagcgttg ttgcagtgca    3240
cggcagatac acttgctgat gcggtgctga ttacgaccgc tcacgcgtgg cagcatcagg    3300
ggaaaacctt atttatcagc cggaaaacct accggattga tggtagtggt caaatggcga    3360
ttaccgttga tgttgaagtg gcgagcgata caccgcatcc ggcgcggatt ggcctgaact    3420
gccagctggc gcaggtagca gagcgggtaa actggctcgg attagggccg caagaaaact    3480
atcccgaccg ccttactgcc gcctgttttg accgctggga tctgccattg tcagacatgt    3540
ataccccgta cgtcttcccg agcgaaaacg gtctgcgctg cgggacgcgc gaattgaatt    3600
atggcccaca ccagtggcgc ggcgacttcc agttcaacat cagccgctac agtcaacagc    3660
aactgatgga aaccagccat cgccatctgc tgcacgcgga agaaggcaca tggctgaata    3720
tcgacggttt ccatatgggg attggtggcg acgactcctg gagcccgtca gtatcggcgg    3780
aattccagct gagcgccggt cgctaccatt accagttggt ctggtgtcaa aaataataat    3840
aaccgggcag gccatgtctg cccgtatttc gcgtaaggaa atccattatg tactattaa    3900 aaaacacaaa cttttggatg ttcggtttat tctttttctt ttactttttt atcatgggag    3960
cctacttccc gttttttccg atttggctac atgacatcaa ccatatcagc aaaagtgata    4020
```

```
cgggtattat ttttgccgct atttctctgt tctcgctatt attccaaccg ctgtttggtc    4080
tgctttctga caaactcgga acttgtttat tgcagcttat aatggttaca aataaagcaa    4140
tagcatcaca aatttcacaa ataaagcatt tttttcactg cattctagtt gtggtttgtc    4200
caaactcatc aatgtatctt atcatgtctg gatcctctag agtcgacctg caggcatgca    4260
agctggcact ggccgtcgt                                                 4279

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
gaatacaaag cttatgcatg                                                  20

<210> SEQ ID NO 3
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 3
gaatacaaag ctt                                                         13

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
aaagcttatg catgcggccg                                                  20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
cggccgcatc tagagggccc                                                  20

<210> SEQ ID NO 6
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 6
gcggccgcat ctagagggcc cggat                                            25

<210> SEQ ID NO 7
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 7
aatacaaagc ttatgcatgc ggcc                                        24

<210> SEQ ID NO 8
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 8
aatacaaagc ttatgcatgc ggccgcatct                                  30

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
catgcataag ctttgtattc                                             20

<210> SEQ ID NO 10
<211> LENGTH: 13
<212> TYPE: DNA
<213> ORGANISM: Artificial Sequence
<220> FEATURE:
<223> OTHER INFORMATION: Synthetic oligonucleotide

<400> SEQUENCE: 10
aagctttgta ttc                                                    13

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
cggccgcatg cataagcttt                                             20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
gggccctcta gatgcggccg                                             20

<210> SEQ ID NO 13
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 13
atccgggccc tctagatgcg gccgc                                       25

<210> SEQ ID NO 14
<211> LENGTH: 24
```

```
<212> TYPE: DNA
<213> ORGANISM: Artificial Sequence
<220> FEATURE:
<223> OTHER INFORMATION: Synthetic oligonucleotide

<400> SEQUENCE: 14
ggccgcatgc ataagctttg tatt                                            24

<210> SEQ ID NO 15
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 15
agatgcggcc gcatgcataa gctttgtatt                                      30

<210> SEQ ID NO 16
<211> LENGTH: 1798
<212> TYPE: RNA
<213> ORGANISM: Unknown
<220> FEATURE:
<223> OTHER INFORMATION: mRNA sequence for Firefly luciferase

<400> SEQUENCE: 16
gaauacaaag cuuaugcaug cggccgcauc uagagggccc ggauccaaau ggaagacgcc     60
aaaaacauaa agaaaggccc ggcgccauuc uauccucuag aggauggaac cgcuggagag    120
caacugcaua aggcuaugaa gagauacgcc cugguccug gaacaauugc uuuuacagau    180
gcacauaucg aggugaacau cacguacgcg aauacuucg aaaugccgu ucgguuggca     240 gaagcuauga aacgauaugg gcugaauaca aaucacagaa ucgucguaug cagugaaaac    300
ucucuucaau ucuuuaugcc gguguuggc gccguuauuu ucggaguug caguugcgcc    360 cgcgaagcac auuuauaaug aacgugaauu gcucaacagu augaacauuu cgcagccuac    420
cguaguguuu guuccaaaa aggguugca aaaaauuuug aacgugcaaa aaaaauuacc    480
aauaauccag aaaauuauua ucauggauuc uaaaacggau uaccagggau uucagucgau    540
guacacguuc gucacaucuc aucuaccucc cgguuuuaau gaauacgauu uguaccaga    600 guccuuugau cgugacaaaa caauugcacu gauaaugaau uccucuggau cuacgggguu    660
accuaagggu guggcccuuc cgcauagaac ugccugcguc agauucgc augccagaga    720 uccuauuuuu ggcaaucaaa ucauuccgga uacugcgauu uuaaguguug uuccauucca    780
ucacgguuuu ggaauguuua cuacacucgg auauuugaua uggauuuc gagcgcucuu    840 aauguauaga uuugaagaag agcuguuuuu acgaucccuu caggauuaca aaauucaaag    900
ugcguugcua uaccaaccc uauuuucauu cuucgccaaa agcacucuga uugacaaaua    960
cgauuuaucu aauuuacacg aaauugcuuc ugggggcgca ccucuuucga agagucgg    1020 ggaagcgguu gcaaaacgcu uccaucuucc agggauacga caaggauaug gcucacuga    1080 gacuacauca gcuauucuga uuacacccga ggggaugau aaaccgggcg cggucgguaa    1140
aguuguucca uuuuuugaag cgaagguugu ggaucggau accgggaaaa cgcugggcgu    1200
uaaucagaga ggcgaauuau gugucagagg accuaugauu augucggu auguaaacaa    1260 uccggaagcg accaacgccu ugauugacaa ggaugaugg cuacauucug agacauagc    1320 uuacugggac gaagacgaac acuucuucau aguugaccgc uugaagucuu uaauuaaaua    1380
caaaggauau caggugggcc ccgcugaauu ggaaucgaua uuguuacaac accccaacau    1440
```

```
cuucgacgcg ggcguggcag gucuucccga cgaugacgcc ggugaacuuc ccgccgccgu    1500
uguuguuuug gagcacggaa agacgaugac ggaaaaagag aucguggauu acgucgccag    1560
ucaaguaaca accgcgaaaa aguugcgcgg aggaguugug uuuguggacg aaguaccgaa    1620
aggucuuacc ggaaaacucg acgcaagaaa aaucagagag auccucauaa aggccaagaa    1680
gggcggaaag uccaaauugu aaaauguaac uguauucagc gaugacgaaa uucuuagcua    1740
uuguaauccu ccgaggggc gagcucccaa aaaaaaaaa aaaaaaaaaa aaaaaaa        1798
```

<210> SEQ ID NO 17
<211> LENGTH: 12
<212> TYPE: DNA
<213> ORGANISM: Consensus Kozack sequence

<400> SEQUENCE: 17

```
gccgccgcca tg                                                          12
```

<210> SEQ ID NO 18
<211> LENGTH: 13
<212> TYPE: DNA
<213> ORGANISM: Consensus Kozack sequence

<400> SEQUENCE: 18

```
gccgccrcca ugg                                                         13
```

<210> SEQ ID NO 19
<211> LENGTH: 8
<212> TYPE: RNA
<213> ORGANISM: Consensus Shine-Dalgarno sequence

<400> SEQUENCE: 19

```
uaaggagg                                                                8
```